United States Patent [19]

Pearlman

[11] Patent Number: 4,739,078

[45] Date of Patent: Apr. 19, 1988

[54] USE OF BOROHYDRIDE-SALT LANTHANIDE SALT REAGENTS FOR STEREO SELECTIVE REDUCTION OF C-15-KETO PROSTAGLANDIN PRECURSORS

[75] Inventor: Bruce A. Pearlman, Kalamazoo, Mich.

[73] Assignee: The Upjohn Company, Kalamazoo, Mich.

[21] Appl. No.: 581,471

[22] Filed: Feb. 17, 1984

[51] Int. Cl.[4] .............................................. C07D 307/93
[52] U.S. Cl. ...................................... 549/305; 549/60; 546/269
[58] Field of Search .................. 549/305, 60; 546/269

[56] References Cited

U.S. PATENT DOCUMENTS

| | | | |
|---|---|---|---|
| 3,706,789 | 12/1972 | Bergstrom et al. | 260/488 |
| 3,965,116 | 6/1976 | Cram | 546/49 |
| 4,052,446 | 10/1977 | Holland et al. | 260/514 |
| 4,301,164 | 11/1981 | Ohno et al. | 424/263 |

OTHER PUBLICATIONS

Grieco et al., J. Org. Chem., vol. 44, 1979, pp. 2194–2199.
Gemal et al., J. Amer. Chem. Soc., 103:5454 (1981).
Luche, J. Amer. Chem. Soc., 100:2226 (1978).

*Primary Examiner*—Jane T. Fan
*Attorney, Agent, or Firm*—Lawrence T. Welch

[57] ABSTRACT

The present invention provides a novel process for reducing 15-keto prostaglandin intermediates. This process stereospecifically reduces these 15-keto intermediates using sodium borohydride and ceriumtrichloride, yielding a predominance of the 15α epimer.

2 Claims, No Drawings

USE OF BOROHYDRIDE-SALT LANTHANIDE SALT REAGENTS FOR STEREO SELECTIVE REDUCTION OF C-15-KETO PROSTAGLANDIN PRECURSORS

DESCRIPTION

BACKGROUND OF THE INVENTION

The present invention provides a novel process for preparing intermediates for known compounds. More particularly, the present invention provides an improved means for stereoselectively reducing known bicyclic lactone prostaglandin precursors in the preparation of prostaglandins. This reduction is undertaken using a borohydride salt and a trivalent lanthanide salt.

The prostaglandins are a family of compounds which are derivatives of prostanoic acid. (See, e.g., Bergstrom, et al., Pharmacol. Rev. 20: 1 (1968), and references cited therein.) A trivial system of nomenclature has been devised for this class of compounds, see, N. A. Nelson, Journal of Medicinal Chemistry, 17: 911 (1974). This system of nomenclature is used below.

The prostaglandins are known to be useful for a wide variety of pharmaceutical purposes including decreasing blood pressure, stimulating smooth muscles, inhibiting gastric secretion and protecting gastric mucosa, controlling spasms and facilitating breathing in asthmatic conditions, decongesting nasal passages, decreasing blood platelet adhesion and inhibiting blood platelet aggregation and thrombus formation, and a variety of uses in the reproductive area including labor induction, abortion, cervical dilatation, estrus regulation, and menstrual regulation. For a recent discussion of prostaglandins which are currently being developed commercially, see N. A. Nelson, et al., Chemical and Engineering News, pp. 30–44 (Aug. 16, 1982).

Initially, the prostaglandins were isolated from natural materials. However, several routes for the total chemical synthesis of the prostaglandins are now known. See, e.g. E. J. Corey, et al., J. Am. Chem. Soc. 91: 5675 (1969); E. J. Corey, et al., J. Am. Chem. Soc. 92: 397 (1970); and U.S. Pat. No. 3,711,515. These and many other prostaglandin synthetic methods proceed through a bicyclic lactone intermediate such as that of the Formula I.

Most of the commercially important prostaglandins are of the "natural" configuration, i.e., the same stereochemical configuration as the prostaglandins produced in mammalian matabolism. In particular, the stereochemical configuration of the hydroxy group at the 15-position of many of the commercially important prostaglandins is natural (i.e., alpha).

Two such commercially important prostaglandins are $PGF_2\alpha$ (see U.S. Pat. No. 3,706,789), which is marketed by The Upjohn Company for estrous synchronization, and 11-deoxy-11,16,16-trimethyl-$PGE_2$ (see U.S. Pat. No. 4,052,446), a proposed anti-ulcer drug of Hoffmann-LaRoche, Inc.

In certain of the synthetic schemes for the preparation of prostaglandins, intermediates such as that of the Formula I are prepared from the corresponding ketones such as that of the Formula II. While numerous means exist for the reduction of this ketone, many are not stereospecific, i.e., they result in a mixture of epimers wherein the hydroxy group is in the alpha or beta position.

A number of reagents stated to be effective for stereoselective reduction of the 15-position of prostaglandins have been described. Thus, diisobutylaluminum 2,6-di-t-butyl-4-methylphenoxide (DIBAL-BHT) has been described in Iguchi, et al., Bull. Chem. Soc. Japan, 54: 3033 (1981), and Iguchi, et al., J. Org. Chem., 44: 1363 (1979). Certain lithium aluminum hydride compounds have been disclosed for this purpose in U.S. Pat. No. 4,284,581 and Noyori, et al., J. Amer. Chem. Soc. 101: 5843 (1979); and Noyori, Pure Appl. Chem. 53: 2315 (1981). Lithium thexyl limonyl borohydride (formed by treatment of limonene with thexyl borane and t-BuLi) is utilized in Corey, et al., J. Amer. Chem. Soc. 94: 8616 (1972). Lithium methyldiisopinocamphenyl borohydide and lithium-t-butyl-diisopinocamphenyl borohydride are employed in Corey, et al., J. Amer. Chem. Soc. 93: 1491 (1971). German Offen. No. 2,257,162 discloses the use of sodium cyanodiisopinocamphenyl brohydride. U.S. Pat. No. 4,247,635 discloses the use of certain microbes for this reduction. Hutton, et al., Syn. Com. 9: 799 (1979) discloses the use of various reagents produced by treatment of 3-O-benzyl-monocyclohexanone glucose with 1.0 equiv. lithium aluminumhydride and 1.0 equiv. of a monohydroxylic compound such as ethanol, adamantyl alcohol, and adamantylmethyl alcohol. British Pat. No. 1,498,764 discloses the use of potassium trialkyl borohydrides.

However, while each of these reagents is effective for stereospecific reduction of particular prostaglandin intermediates, none is effective for all such compounds. Moreover, many of these reagents are optically active, which means that their use is limited to optically active prostanoid enone substrates. Further, none of these reagents is effective for the stereoselective reduction of a prostaglandin intermediate such as that of the Formula III. In addition, the reagents noted above are quite expensive and produce product mixtures from which the product can be isolated only with some difficulty. The only exception is DIBAL/BHT, which, as noted below, is not effective for stereoselective reduction of a compound of the Formula III.

PRIOR ART

A number of stereoselective reducing agents have been described, as noted above. 11-Deoxy-11,16,16-trimethyl-$PGE_2$ is disclosed in U.S. Pat. No. 4,052,446. $PGF_2\alpha$ is disclosed in U.S. Pat. No. 3,706,789. The use of sodium borohydride in the presence of cerium trichloride-trihydrate as a reducing agent is disclosed in Luche, J. Amer. Chem. Soc. 100: 2226 (1978) and Gemal, et al., J. Amer. Chem. Soc. 103: 5454 (1981). However, these references do not describe a stereoselective reduction of prostaglandins using this method. U.S. Pat. No. 4,301,164, (column 25), discloses the use of cerium trichloride and sodium borohydride for reduction of certain prostanoid C-15 ketones that are susceptible to 13,14-double bond saturation with conventional reagents such as $Zn(BH_4)_2$. However, this patent does not describe a stereoselective reduction ($\alpha/\beta$ is 43/57: See Example 97).

SUMMARY OF THE INVENTION

The present invention particularly provides:
a process for the stereospecific reduction of a compound of the Formula A-1 to a compound of the Formula A-2
wherein $R_1$ is
(a) methyl, or
(b) $OR_{18}$;

wherein $L_1$ is
  (a) $\alpha$-$R_9$: $\beta$-$R_{10}$;
  (b) $\alpha$-$R_{10}$: $\beta$-$R_9$;
  (c) $\alpha$-$OR_8$: $\beta$-$R_7$; or
  (d) $\alpha$-$R_7$: $\beta$-$OR_8$;
wherein $R_1$ is ($C_1$-$C_4$)alkyl;
wherein $R_2$ is
  (a) —O—(PhX);
  (b) —$C_pH_{2p}$—(PhX);
  (c) —$C_mH_{2m}$—(DZ);
  (d) —$C_pH_{2p+1}$;
  (e) —$CH_2$—$CH_2$—$CH$=$C(CH_3)_2$;
  (f) —O—(T); or
  (g) —$C_pH_{2p}$—(Py);
wherein (PhX) is phenyl substituted by zero to 3 of the following:
  (a) ($C_1$-$C_4$)alkyl
  (b) chloro;
  (c) fluoro;
  (d) bromo;
  (e) nitro;
  (f) trifluoromethyl; or
  (g) $OR_8$;
wherein DZ is a ($C_3$-$C_6$)cycloaliphatic substituted by zero to 3 of the following:
  (a) ($C_1$-$C_4$)alkyl;
  (b) chloro;
  (c) fluoro;
  (d) bromo;
  (e) nitro;
  (f) trifluoromethyl; or
  (g) $OR_8$;
wherein T is 3-thienyl;
wherein Py is 2, 3, or 4-pyridinyl;
wherein $R_7$ is
  (a) hydrogen, or
  (b) $C_1$-$C_4$ alkyl;
wherein each occurrence of $R_8$ is the same or different and is
  (a) hydrogen;
  (b) ($C_1$-$C_4$)alkyl; or
wherein $R_9$ and $R_{10}$ are the same or different and are
  (a) hydrogen;
  (b) ($C_1$-$C_4$)alkyl; or
  (c) fluoro;
wherein $R_{13}$ is
  (a) hydrogen;
  (b) ($C_1$-$C_{12}$)alkyl;
  (c) ($C_3$-$C_{10}$)cycloalkyl;
  (d) ($C_7$-$C_{12}$)aralkyl;
  (e) phenyl; or
  (f) substituted phenyl;
wherein $R_{17}$ is ($C_1$-$C_4$)alkyl;
wherein $Y_1$ is
  (a) a valence bond; or
  (b) —$(CH_2)_r$;
wherein p is an integer from 0–8;
wherein a is an integer from 0–2;
wherein b is an integer from 1–5;
wherein $R_{18}$ is a protecting group; which comprises treating the A-1 compound with a borohydride salt in the presence of a trivalent lanthanide salt.

Formula A-1, as depicted, may exist in optically pure form or as a racemic mixture. Both are intended to be included in the process of this invention.

In Formulas A-1 and A-2, when $R_1$ is methyl, $R_2$ is $nC_4H_9$, and $L_1$ is $\alpha$-$CH_3$: $\beta$-$CH_3$, the compound is used to prepare 11-deoxy-11,16,16-trimethyl-$PGE_2$. When $R_1$ is $OR_{18}$, $R_2$ is $nC_4H_9$, and $L_1$ is $\alpha$-H: $\beta$-H, the compound is used to prepare $PGF_{2\alpha}$.

By "borohydride salt" is meant any of the known borohydride salts which are used as reducing agents. These include particularly those formed with metal cations.

Especially preferred cations are those derived from the alkali metals, e.g., lithium, sodium, and potassium, and from the alkaline earth metals, e.g., magnesium and calcium, although cationic forms of other metals as well as organic cations such as quaternary ammonium and quaternary phosphonium are within the scope of this invention. The alkali metal salts, particularly sodium borohydride, are preferred in the instant invention.

By "trivalent lanthanide salt" is meant a trivalent salt formed with any of the following elements: cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Suitable trivalent salts formed with these elements include the halides, (e.g., chloride, bromide, fluoride, iodide), nitrates, sulfates, sulfonates, and phosphates. The chlorides are preferred for use in this invention.

Cerous trichloride ($CeCl_3$) is the most preferred lanthanide salt to be used in this invention because of its realtively low cost and the favorable ratio of $\alpha/\beta$ epimers obtained. Although $SmCl_3$ produces a slightly more favorable $\alpha/\beta$ ratio, this reagent is much more expensive, making it less preferred.

The protecting groups within the scope of $R_{18}$ are any group capable of surviving the conditions of the reaction. These include a group which replaces a hydroxy hydrogen and is neither attacked by nor is as reactive to the reagents used in the transformations used herein as a hydroxy is and which is subsequently replaceable by acid hydrolysis with hydrogen in the preparation of the prostaglandin-type compounds. Many such protective groups are known in the art.

These groups include silyl groups of the formula —$Si(G_1)_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a —$Si(G_1)_3$ moiety the various $G_1$'s are the same or different and at least one $G_1$ is hindered (such as tert-butyl). Silyl groups within the scope of —$Si(G_1)_3$ include triethylsilyl, triisopropyl silyl, triphenylsilyl, t-butyldimethylsilyl, methylphenylbenzylsilyl, and tert-butyl-diphenyl silyl. With regard to $G_1$, examples of alkyl are methyl, ethyl, isopropyl, propyl, isobutyl, butyl, sec-butyl, tert-butyl, pentyl, and the like. Examples of aralkyl are benzyl, phenethyl, $\alpha$-phenylethyl, 3-phenylpropyl, $\alpha$-naphthylmethyl, and 2-($\alpha$-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. $G_1$ may also be a phenoxy group, for example of a silyl protecting group containing a phenoxy group that has been disclosed in the literature is 2,4,6-tri-tert-butylphenoxy dimethylsilyl. Tert-butyldimethylsilyl is most preferred as a silylating agent.

These silyl groups are known in the art. See for example, Pierce "Silylating of Organic Compounds," Pierce Chemical Company, Rockford Ill. (1968). When silylated products of the charts below are intended to be subjected to chromatographic purification, then the use of silyl groups known to be unstable to chromatography is to be avoided.

Also included as protecting groups within the scope of $R_{18}$ are acyl protecting groups, including both aryl and alkyl esters (such as benzoate or p-phenyl-benzoate) and urethanes (such as phenyl urethane p-phenylurethane).

Examples of additional protecting groups within the scope of $R_{18}$ include ether groups such as benzyl, furylmethyl, p-methoxybenzyl, benzhydryl, triphenylmethyl.

The acetal protecting groups within the scope of $R_{18}$ include ethoxy-ethyl, tetrahydropyranyl, benzyloxymethyl, methoxymethyl, dimethylmethoxy methyl, and methylthiomethyl. Also included are: tetrahydropyranyl, substituted tetrahydropyranyl, t-butoxymethyl, ethoxy ethyl, methoxy methyl, and 2-methoxyethoxy-methyl. See for reference E. J. Corey, Proceedings of the Robert A. Welch Foundation Conferences on Chemical Research, XII Organic Synthesis, pgs. 51-79 (1969). Those blocking groups which have been found useful include:

(a) tetrahydropyranyl;
(b) tetrahydrofuranyl;
(c) acid-labile ethers such as tert-butyl or triphenylmethyl; and
(d) a group of the formula —$C(OR_{11})(R_{12})$—$CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are hydrogen or alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —$(CH_2)_a$— or when $R_{12}$ and $R_{13}$ are taken together —$(CH_2)_b$—O—$(CH_2)_c$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{18}$ is tetrahydropyranyl, the tetrahydropyranyl ether derivative of any hydroxy moieties of the intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichometric excess, preferably 4 to 100 times the stoichiometric amount. The reaction is normally complete in less than an hour at 20°-50° C.

When the protective group is tetrahydrofuranyl, 2,3-dihydrofuran is used, as described in the preceding paragraph, in place of the 2,3-dihydropyran.

When the protective group is of the formula —C-$(OR_{11})(R_{12})$—CH—$(R_{13})(R_{14})$, wherein $R_{11}$, $R_{12}$, $R_{13}$, and $R_{14}$ are as defined above; a vinyl ether or an unsaturated cyclic or heterocyclic compound, e.g., 1-cyclohexene-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

The protective groups as defined by $R_{18}$ are removed by mild acidic hydrolysis. For example, by reaction with (1) hydrochloric acid in methanol; (2) a mixture of acetic acid, water, and tetrahydrofuran or (3) aqueous citric acid or aqueous phosphoric acid in tetrahydrofuran, at temperatures below 55° C., hydrolysis of the blocking group is achieved.

The carbon atom content of various hydrocarbon-containing moieties is indicated by a prefix designation the minimum and maximum number of carbon atoms in the moiety, i.e., the prefix ($C_i$–$C_j$) indicates a moiety of the integer "i" to the integer "j" carbon atoms, inclusive. Thus ($C_1$–$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl to 7 to 12 carbon atoms, inclusive, are benzyl, 2-phenyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of substituted benzyl, phenylethyl, or phenylpropyl are (o-, m-, or p-)tolyl, (o-, m-, or p-)ethylphenyl, 2-ethyl-(o-, m-, or p-)tolyl, 4-ethyl-o-tolyl, 5-ethyl-m-tolyl, (o-, m-, or p-)propylphenyl 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6- or 3,5-)dichlorophenyl, 4-chloro-3-fluorophenyl, (3- or 4-(chloro-2-fluorophenyl, (o-, m-, or p-)trifluoro-methylphenyl, (o-, m-, or p-)ethoxyphenyl, (4- or 5-)chloro-2-methoxyphenyl, and 2,4-dichloro-(5- or 6-)methylphenyl.

With regard to the divalent substituents described above (e.g., $L_1$) these divalent radicals are defined as α-$R_i$: β-$R_j$, wherein $R_i$ represents the substituent of the divalent moiety in the alpha configuration with respect to the plane of the ring and $R_j$ represents the substituent of the divalent moiety in the beta configuration with respect to the plane of the ring. Accordingly, when $L_1$ is defined as a-$R_9$: β-$R_{10}$, the $R_9$ or the $L_1$ moiety is in the alpha configuration, and the $R_{10}$ substituent is in the beta configuration.

The reduction of the present invention is depicted in Chart A. In Chart A, an enone compound (either optically active or a racemic mixture) of the Formula A-1 is treated with a borohydride salt (e.g., sodium borohydride) and a lanthanide salt (e.g., cerium trichloride) in an inert solvent at a low temperature to yield the corresponding 15α hydroxy compound. These enones are well-known and readily available to those skilled in the art. For example, the compound of Formula III is disclosed in U.S. Pat. No. 4,052,446. Typically, this procedure employs from about 0.25 to 1.00 moles of borohydride salt and about 0.10 to about 1.00 moles of lanthanide salt per mole of enone. Preferably, about 0.60 moles of borohydride and about 0.25 moles of anthanide are employed. The temperature range used for this reduction is from about −100° to about 0° C. Preferably a temperature in the range of about −78° to about −25° C. is used. It is most preferred to use a temperature in the range of about −78° C. Those skilled in the art can readily convert the Formula A-2 product to the corresponding prostaglandins by means known in the art, (e.g., Corey et al., supra).

DESCRIPTION OF THE PREFERRED EMBODIMENTS

The present invention is seen more fully by the examples given below.

EXAMPLE 1

(Formula A-1: $R_1$ is methyl, $R_2$ is $nC_4H_9$, $L_1$ is α-$CH_3$: b-$CH_3$)

A solution of the optically active enone (15.23 gm, 52.1 mmoles) and cerous chloride heptahydrate ($CeCl_3 \cdot 7H_2O$) (4.86 gm, 13.03 mmoles) in 170 ml methanol and 50 ml methylene chloride is cooled to −78° C. (internal temp. −67° C.) and treated with solid sodium borohydride ($NaBH_4$) (1.097 gm, 29.0 mmoles). The reaction is incomplete after 40 min by TLC, so more $NaBH_4$ (106 mg, 2.82 mmoles) is added. After another 20 min, the reaction is judged to be complete, so it is quenched by addition of 25 ml saturated ammonium chloride ($NH_4Cl$). The reaction mixture is then allowed to warm up to room temperature, poured into 800 ml saturated $NH_4Cl$, and extracted with ethyl acetate (2×500 ml). The extracts are then dried and concentrated to leave 16.30 gm of a pale yellow oil.

In order to determine the 15α/β ratio, a small scale experiment (1.099 gm enone) was carried out by the above described procedure and the crude product mixture was chromatographed on silica gel (gradient elution, methylene chloride to 10% acetone/methylene chloride. The fractions containing the desired 15α isomer (Rf=0.47; eluant: 5% acetone/methylene chloride) were combined and concentrated in vacuo to leave a pale yellow oil (weight: 818 mg, 73.9%). The fractions containing the 15β isomer (Rf=0.30) were then combined and concentrated in vacuo to leave a pale yellow oil (weight: 180 mg, 16.3%). Therefore, the 15α/β ratio is 82:18.

EXAMPLE 2

Comparison of Reducing Agents and Reaction Parameters

The effects of various reaction parameters are set forth in the tables below. In all cases, the enone A-I is optically active, $R_1$ is $CH_3$, $L_1$ is $(CH_3)_2$, and $R_2$ is $nC_4H_9$.

TABLE I

| Reducing Agent/ Temp (°C.) | A-1 | A-2 | 15-epi-A-2 | 15 α/β | 13,14-Di hydro-A-2 (α/β) | IV, 15-epi-IV (α/β) |
|---|---|---|---|---|---|---|
| $NaBH_4$, MeOH,/ 0° | trace | 50.6 | 32.3 | 61.0/39.0 | 6.1 (52/48) | 1.9 (63/37) |
| DIBAL/BHT, ØMe,/−24° | trace | 50.5 | 49.5 | 50.5/49.5 | <1.0% | trace |
| $NaBH_4$, $CeCl_3$ MeOH, /−78° | .10 | 78.6 | 17.0 | 82.3/17.7 | .04 (—) | .60 (70/30) |

TABLE II (Effect of Co-solvent on Product, 0.25 equiv. $CeCl_3$, −78°)

| Solvents | A-1 | A-2 | 15-epi-A-2 | 15 α/β | 13,14-Di-hydro (α/β) | IV, 15-epi-IV (α/β) |
|---|---|---|---|---|---|---|
| MeOH | .10 | 78.6 | 17.0 | 82.3/17.7 | .04 (—) | .60 (70/30) |
| MeOH/ THF | <.1 | 75.9 | 19.6 | 79.5/20.5 | <.1 | 4.4 (79/21) |
| MeOH/ $CH_2Cl_2$ | 1.7 | 77.8 | 15.2 | 83.7/16.3 | <.1 | 1.9 (81/19) |

TABLE III (Effect of Temperature on Product Distribution; .25 equiv. $CeCl_3$)

| Solvents/ Temp. (°C.) | A-1 | A-2 | 15-epi-A-2 | 15 α/β | 13,14-Di-hydro-A-2 (α/β) | Triols (α/β) |
|---|---|---|---|---|---|---|
| MeOH, $CH_2Cl_2$/ −78° | 1.7 | 77.8 | 15.2 | 83.7/16.3 | <.1 | 1.9 (81/19) |
| MeOH, $CH_2Cl_2$/ −30° | 2.5 | 65.5 | 20.12 | 76.4/23.6 | <.1 | 5.2 (77/23) |
| EtOH, $CH_2Cl_2$/ −20° | 3.9 | 73.1 | 19.9 | 78.6/21.4 | .7 | 3.5 (77/23) |

EXAMPLE 3

Cerium Borohydride Reduction

A solution of the optically active Formula A-1 enone, wherein $R_1$ is $CH_3$, $R_2$ is $nC_4H_9$, and $L_1$ is α-$CH_3$: β-$CH_3$ (8.297 g, 28.42 mmoles), and cerous chloride heptahydrate (2.651 g, 7.115 mmoles) in 80 ml methanol and 50 ml methylene chloride is cooled to −76° C. To the resulting cloudy solution is then added solid sodium borohydride (0.650 g, 17.113 mmoles) all at once. The reaction mixture is then stirred at −76° C. until a TLC (eluant: 40% ethyl acetate/cyclohexane) indicates that the amount of product (Rf=0.38) is maximal (60 min; at this point roughly equal amounts of unreacted enone (Rf=0.50) and the triol C-15 epimer pair [IV, Rf=0.10 and 15-epi-IV, Rf=0.05] are present). The reaction mixture is then quenched with 50 ml saturated aqueous ammonium chloride ($NH_4Cl$), allowed to warm to room temperature, poured into 400 ml saturated aqueous NH₄Cl, and extracted with ethyl acetate (2×200 ml). The extracts are then washed successively with 100 ml saturated aqueous NH₄Cl and 100 ml saturated aq. sodium chloride, dried over magnesium sulfate, and concentrated in vacuo to leave a pale yellow oil, consisting of a 83.7:15.6 mixture of the desired product A-2 ($R_1$ is $CH_3$, $R_2$ is $nC_4H_9$ and $L_1$ is α-$CH_2$: β-$CH_3$) and its epimer (by HPLC).

The desired product weighs 8.468 g.

EXAMPLE 4

The optically active enone of Formula A-1, wherein $R_1$ is $CH_3$, $R_2$ is $nC_4H_9$, and $L_1$ is α-$CH_3$: β-$CH_3$ is treated with sodium borohydride in the presence of all but the four most expensive lanthanide trichloride hydrates (Pm, Ho, Tm, and Lu) under the conditions of Example 3. The results are set forth in Table IV.

TABLE IV

Effect of Lanthanide on Product Distribution

| Lanthanide | Ratio α/β |
|---|---|
| None | 61.0/39.0 (1,2/1,4 = 94/6) |
| Ce | 84.3/15.7 |
| Pr | 84.3/15.7 |
| Nd | 83.0/17.0 |
| Sm | 85.4/14.6 |
| Eu | 79.6/20.4 |
| Gd | 84.0/16.0 |
| Tb | 80.5/19.5 |
| Dy | 81.4/18.6 |
| Er | 81.2/18.8 |
| Yb | 78.9/21.1 |

EXAMPLE 5

A comparison of the results of reduction of optically active racemic enones A-1 ($R_1$ is SitBuMe₂, $R_2$ is $nC_4H_9$ and $L_1$ is α-H: β-H) to A-2.

The results are set forth in Table V

TABLE V

| Substrate | 15 α/β |
|---|---|
| optically active | 70.9/29.1 |
| racemic | 71.6/28.4 |

FORMULAS

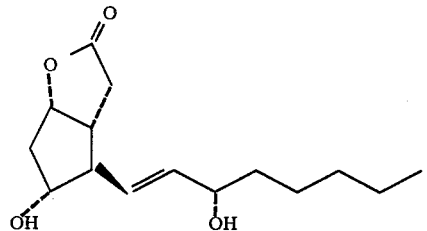

I

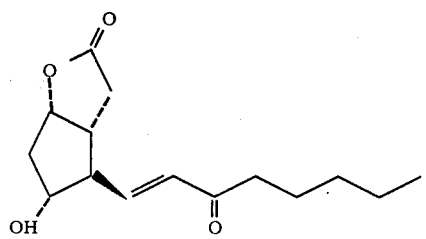

II

-continued
FORMULAS

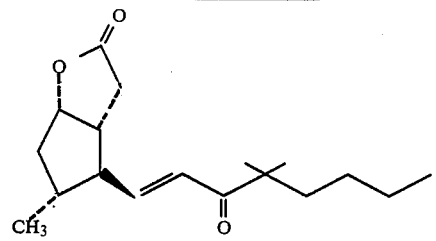

III

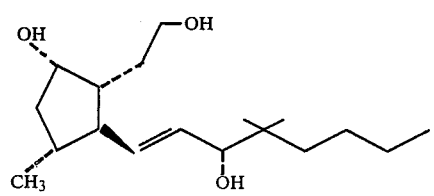

IV

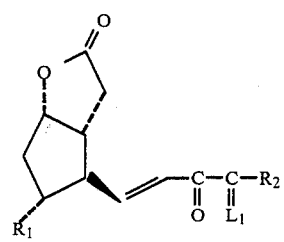

A-1

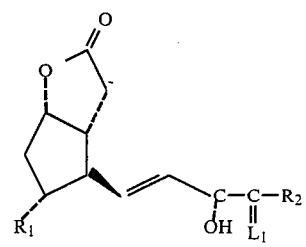

A-2

CHART A

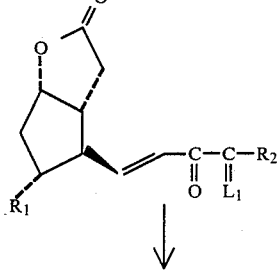

A-1

↓

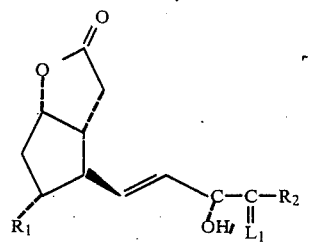

A-2

I claim:
1. A process for sterospecifically reducing a compound of the formula A-1 to a compound of the formula A-2,

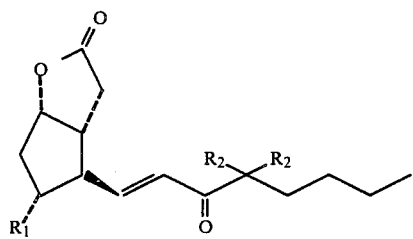
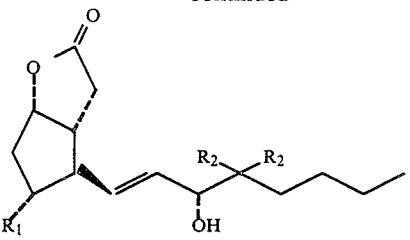
wherein $R_1$ and $R_2$ are methyl, which comprises treating the A-1 compound with a borohydride salt in the presence of a cerous trichloride.
2. A process of claim 1, wherein the borohydride salt is sodium borohydride.
* * * * *